(12) United States Patent
Gliner

(10) Patent No.: US 12,324,770 B2
(45) Date of Patent: Jun. 10, 2025

(54) COMPENSATING FOR IMPERFECT BEHAVIOR OF MULTI-PIEZOELECTRIC CRYSTAL

(71) Applicant: JOHNSON & JOHNSON SURGICAL VISION, INC., Irvine, CA (US)

(72) Inventor: Vadim Gliner, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 649 days.

(21) Appl. No.: 17/231,450

(22) Filed: Apr. 15, 2021

(65) Prior Publication Data
US 2022/0331159 A1    Oct. 20, 2022

(51) Int. Cl.
*A61F 9/007*    (2006.01)
*A61B 17/00*   (2006.01)

(52) U.S. Cl.
CPC .............. *A61F 9/00745* (2013.01); *A61B 2017/00725* (2013.01); *B06B 2201/76* (2013.01)

(58) Field of Classification Search
CPC ...... A61F 9/00745; G01H 9/00; G01H 19/00; A61C 17/20; A61C 1/07; B06B 201/40; B06B 2201/55; A61B 2017/00725
See application file for complete search history.

(56) References Cited

U.S. PATENT DOCUMENTS

| | | | |
|---|---|---|---|
| 2,434,480 A | 1/1948 | Anderson | |
| 3,941,122 A | 3/1976 | Jones | |
| 3,964,487 A | 6/1976 | Judson | |
| 3,990,452 A | 11/1976 | Murry et al. | |
| 4,126,137 A | 11/1978 | Archibald | |
| 4,184,510 A | 1/1980 | Murry et al. | |
| 4,808,948 A | 2/1989 | Patel et al. | |
| 4,827,911 A | 5/1989 | Broadwin et al. | |
| 4,849,872 A | 7/1989 | Gassler | |
| 4,861,332 A | 8/1989 | Parisi | |
| 4,954,960 A | 9/1990 | Lo et al. | |

(Continued)

FOREIGN PATENT DOCUMENTS

| | | |
|---|---|---|
| CN | 109029690 A | 12/2018 |
| CN | 111557784 B | 11/2020 |

(Continued)

OTHER PUBLICATIONS

Edelman et al., A stroboscopic Vibration Analyzer, Journal of Research of the National Bureau of Standards-C. Engineering and Instrumentation; vol. 63C, No. 2; p. 97; Oct.-Dec. 1959. (Year: 1959).*

(Continued)

*Primary Examiner* — Daniel J Colilla

(57) ABSTRACT

A method for calibrating a probe includes applying respective harmonic electrical signals having respective amplitudes and respective phases to multiple piezoelectric crystals coupled with a tip of the probe so as to cause the tip to vibrate, observing a motion of the tip while applying the respective harmonic electrical signals, adjusting the respective amplitudes and the respective phases of the signals so as to cause the observed motion of the tip to conform to a predefined trajectory, and recording an indication of the respective, adjusted amplitudes and phases in a memory contained in the probe.

10 Claims, 2 Drawing Sheets

(56) References Cited

U.S. PATENT DOCUMENTS

| | | | |
|---|---|---|---|
| 4,970,656 A | 11/1990 | Lo et al. | |
| 4,983,901 A | 1/1991 | Lehmer | |
| 5,001,649 A | 3/1991 | Lo et al. | |
| 5,026,387 A | 6/1991 | Thomas | |
| 5,062,827 A | 11/1991 | Wiksell | |
| 5,160,317 A | 11/1992 | Costin | |
| 5,162,044 A | 11/1992 | Gahn et al. | |
| 5,209,221 A | 5/1993 | Riedlinger | |
| 5,279,547 A | 1/1994 | Costin | |
| 5,318,563 A | 6/1994 | Malis et al. | |
| 5,331,951 A | 7/1994 | Kepley | |
| 5,370,602 A | 12/1994 | Kepley | |
| 5,388,569 A | 2/1995 | Kepley | |
| 5,406,503 A | 4/1995 | Williams et al. | |
| 5,417,246 A | 5/1995 | Perkins et al. | |
| 5,431,664 A | 7/1995 | Ureche et al. | |
| 5,453,087 A * | 9/1995 | Malinowski | A61F 9/00745 604/22 |
| 5,520,633 A | 5/1996 | Costin | |
| 5,547,459 A | 8/1996 | Kaufman et al. | |
| 5,582,578 A | 12/1996 | Zhong et al. | |
| 5,591,127 A | 1/1997 | Barwick, Jr. et al. | |
| 5,700,240 A | 12/1997 | Barwick, Jr. et al. | |
| 5,733,256 A | 3/1998 | Costin | |
| 5,800,365 A | 9/1998 | Zhong et al. | |
| 5,808,396 A | 9/1998 | Boukhny | |
| 5,843,109 A | 12/1998 | Mehta et al. | |
| 5,852,794 A | 12/1998 | Staggs | |
| 5,979,494 A | 11/1999 | Perkins et al. | |
| 5,997,528 A | 12/1999 | Bisch et al. | |
| 6,010,496 A | 1/2000 | Appelbaum et al. | |
| 6,161,545 A | 12/2000 | Chow | |
| 6,203,516 B1 | 3/2001 | Kepley | |
| 6,394,974 B1 | 5/2002 | Kadziauskas et al. | |
| 6,402,769 B1 | 6/2002 | Boukhny | |
| 6,740,058 B2 | 5/2004 | Lal et al. | |
| 6,986,753 B2 | 1/2006 | Bui | |
| 6,997,935 B2 | 2/2006 | Anderson et al. | |
| 7,554,343 B2 | 6/2009 | Bromfield | |
| 7,713,202 B2 | 5/2010 | Boukhny et al. | |
| 7,758,538 B2 | 7/2010 | Boukhny et al. | |
| 7,811,255 B2 | 10/2010 | Boukhny et al. | |
| 8,195,286 B2 | 6/2012 | Kadziauskas et al. | |
| 8,303,613 B2 | 11/2012 | Crandall et al. | |
| 8,439,938 B2 | 5/2013 | Moore, Jr. | |
| 9,018,887 B2 | 4/2015 | Paschke | |
| 9,050,627 B2 | 6/2015 | Jacobson | |
| 9,393,152 B2 | 7/2016 | Wong et al. | |
| 9,433,723 B2 | 9/2016 | Steen et al. | |
| 10,052,227 B2 | 8/2018 | Saimovici | |
| 10,182,940 B2 | 1/2019 | Chandrakant et al. | |
| 10,363,166 B2 | 7/2019 | Raney | |
| 10,478,336 B2 | 11/2019 | Bromfield et al. | |
| 10,478,533 B2 | 11/2019 | Borgmeier et al. | |
| 10,596,032 B2 | 3/2020 | Raney | |
| 10,596,033 B2 | 3/2020 | Urich et al. | |
| 10,857,030 B2 | 12/2020 | Raney | |
| 11,266,384 B2 | 3/2022 | Christopher et al. | |
| 2001/0003155 A1 | 6/2001 | Rockley et al. | |
| 2002/0193817 A1 | 12/2002 | Lal et al. | |
| 2004/0092921 A1 | 5/2004 | Kadziauskas et al. | |
| 2006/0079788 A1 | 4/2006 | Anderson et al. | |
| 2006/0195077 A1 | 8/2006 | Kadziauskas et al. | |
| 2009/0005712 A1 | 1/2009 | Raney | |
| 2009/0118751 A1 | 5/2009 | Wiener et al. | |
| 2011/0196404 A1 | 8/2011 | Dietz et al. | |
| 2012/0022434 A1 * | 1/2012 | Lue | A61F 9/00763 604/22 |
| 2012/0065578 A1 | 3/2012 | Zhou | |
| 2012/0072197 A1 | 3/2012 | Ovchinnikov | |
| 2012/0143233 A1 | 6/2012 | Sinelnikov | |
| 2012/0150075 A1 | 6/2012 | Ludwin et al. | |
| 2012/0232466 A1 | 9/2012 | Kuebler et al. | |
| 2013/0012868 A1 | 1/2013 | Gordon et al. | |
| 2013/0131692 A1 | 5/2013 | Kadziauskas et al. | |
| 2013/0314077 A1 | 11/2013 | Okada et al. | |
| 2014/0024969 A1 | 1/2014 | Govari et al. | |
| 2014/0163455 A1 | 6/2014 | Wilson et al. | |
| 2014/0257172 A1 | 9/2014 | Yalamanchili | |
| 2015/0133950 A1 | 5/2015 | Shelton et al. | |
| 2016/0346519 A1 | 12/2016 | Bagwell et al. | |
| 2017/0312129 A1 | 11/2017 | Kadziauskas et al. | |
| 2018/0207330 A1 | 7/2018 | Ovchinnikov et al. | |
| 2019/0099547 A1 | 4/2019 | Mehta et al. | |
| 2019/0133822 A1 | 5/2019 | Banko | |
| 2019/0321222 A1 | 10/2019 | Lieu | |
| 2020/0100851 A1 | 4/2020 | Marcuk | |
| 2021/0361481 A1 | 11/2021 | Gliner et al. | |
| 2022/0160543 A1 | 5/2022 | Gliner et al. | |
| 2022/0192878 A1 | 6/2022 | Algawi et al. | |
| 2023/0149213 A1 | 5/2023 | Fuchs | |
| 2023/0338190 A1 | 10/2023 | Fuchs et al. | |

FOREIGN PATENT DOCUMENTS

| | | | |
|---|---|---|---|
| DE | 232755 A1 | 2/1986 | |
| DE | 3910200 A1 | 10/1990 | |
| EP | 0270819 A2 | 6/1988 | |
| EP | 0955984 B1 | 4/2004 | |
| EP | 1990032 A1 | 11/2008 | |
| EP | 3146946 A1 | 3/2017 | |
| EP | 3007660 B1 | 5/2017 | |
| IE | 920003 A1 | 7/1992 | |
| JP | H0796000 A | 4/1995 | |
| WO | 0064388 A1 | 11/2000 | |
| WO | 0152782 A1 | 7/2001 | |
| WO | 2009073859 A1 | 6/2009 | |
| WO | 2016191517 A1 | 12/2016 | |

OTHER PUBLICATIONS

Zhu et al.; Modeling of piezoelectric stack actuators considering bonding layers; Nov. 2015; Journal of Intelligent Material Systems and Structures; vol. 26; Issue 17; pp. 2418-2427. (Year: 2015).*

Leang K.K., et al., "Feedback-Linearized Inverse Feedforward for Creep, Hysteresis, and Vibration Compensation in AFM Piezoactuators," IEEE Transactions on Control Systems Technology, Sep. 1, 2007, vol. 15(5), pp. 927-935.

Chu., et al., "Ins and Outs, Get the Most Out of Today's Advanced Phaco Systems", Cataract & Refractive Surgery Today, Jan. 2016, pp. 40-45.

Castellanos-Gomez, Andres, et al. "Calibration of piezoelectric positioning actuators using a reference voltage-to-displacement transducer based on quartz tuning forks." arXiv preprint arXiv:1203.5767 (2012).

Baggia, S. "Double-frequency stroboscopic method for absolute calibration of vibration transducers." Journal of Sound and Vibration 20.1 (1972): 59-69.

Wikimedia Foundation., "Linear Variable Differential Transformer," Oct. 23, 2023, 3 pages. Retrieved from the Internet: [URL:https://en.wikipedia.org/wiki/ Linear_variable_differential_transformer].

* cited by examiner

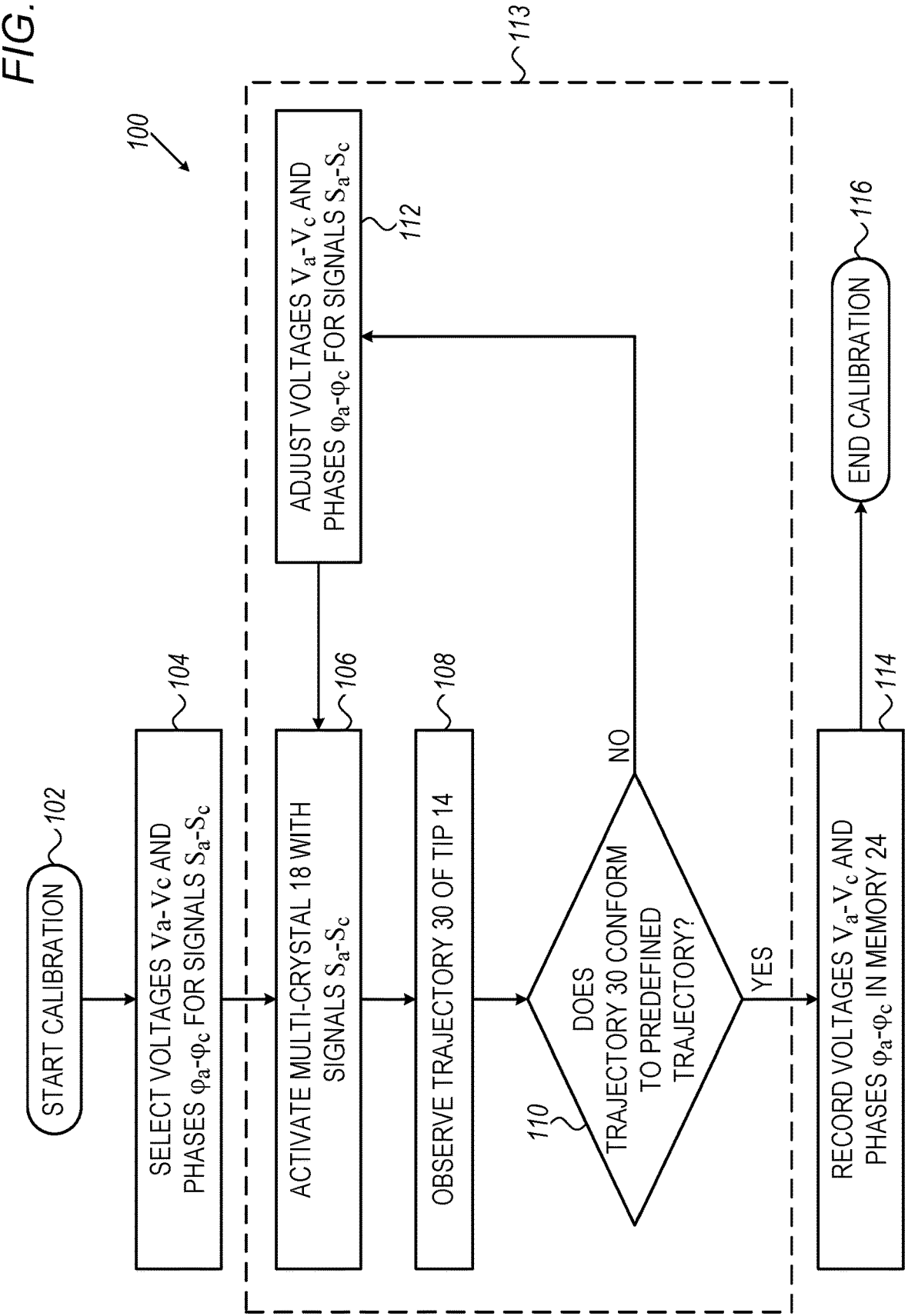

COMPENSATING FOR IMPERFECT BEHAVIOR OF MULTI-PIEZOELECTRIC CRYSTAL

FIELD OF THE INVENTION

The present invention relates generally to piezoelectric-vibration-based medical devices, and particularly to phacoemulsification systems.

BACKGROUND

A cataract is a clouding and hardening of the eye's natural lens, a structure which is positioned behind the cornea, iris and pupil. The lens is made up mostly of water and protein, and as people age these proteins change and may begin to clump together, obscuring portions of the lens. Phacoemulsification cataract surgery can be used to correct this condition. In this procedure, a surgeon makes a small incision in the sclera or cornea of the eye. Then a portion of the anterior surface of the lens capsule is removed to gain access to the cataract. The surgeon then inserts the tip of a phacoemulsification probe into the lens capsule. The tip vibrates at ultrasonic frequency to sculpt and emulsify the cataract while a pump aspirates particles and fluid from the eye through the tip. Aspirated fluids are replaced with irrigation of a balanced salt solution to maintain the anterior chamber of the eye. After removing the cataract with phacoemulsification, the softer outer lens cortex is removed with suction. An intraocular lens (IOL) is then introduced into the empty lens capsule to restore the patient's vision.

For safe, efficient phacoemulsification, it is important that the vibration of the tip of the probe be precisely controlled. For this purpose, for example, U.S. Pat. No. 9,050,627 describes a method for determining the voltage current phase relationship of a piezoelectric phacoemulsification handpiece. The method includes the steps of obtaining an analog AC voltage signal corresponding to the operating AC voltage of a piezoelectric handpiece along with an analog AC current signal corresponding to the operating AC current of the piezoelectric handpiece. Using reference detection circuits, a digital voltage signal and a digital current signal is produced.

U.S. Pat. No. 5,406,503 describes an electronic control system for determining the resonant frequency of and driving ultrasonic transducers in a phacoemulsification probe used for ophthalmic surgery. The control system includes a voltage-controlled oscillator, power amplifier, power monitor, and automatic gain control circuit operating under the direction of command signals received from a microprocessor-based control console.

Stroboscopic techniques have been used for optical determination of vibration amplitude for the purpose of calibrating vibration transducers. For example, Baggia describes a technique of this sort in an article entitled "Double-frequency stroboscopic method for absolute calibration of vibration transducers," published in the *Journal of Sound and Vibration*, 20:1 (1972), pages 59-69.

SUMMARY

Embodiments of the present invention that are described hereinbelow provide improved methods for calibrating vibrating probes, as well as probes that are produced by such methods.

There is therefore provided, in accordance with an embodiment of the present invention, a method for calibrating a probe. The method includes applying respective harmonic electrical signals having respective amplitudes and respective phases to multiple piezoelectric crystals coupled with a tip of the probe so as to cause the tip to vibrate, observing a motion of the tip while applying the respective harmonic electrical signals, adjusting the respective amplitudes and the respective phases of the signals so as to cause the observed motion of the tip to conform to a predefined trajectory, and recording an indication of the respective, adjusted amplitudes and phases in a memory contained in the probe.

In a disclosed embodiment, the method further includes reading and applying the recorded indication from the memory in order to cause the probe to vibrate along the predefined trajectory in a clinical procedure. Additionally, the clinical procedure includes phacoemulsification of a lens of an eye of a patient, and applying the recorded indication includes inserting the tip into a lens capsule of an eye, and vibrating the tip so as to emulsify the lens.

In an additional embodiment, the predefined trajectory is circular.

In a further embodiment, adjusting the respective amplitudes and the respective phases includes adjusting and recording the respective amplitudes and the respective phases for a plurality of different trajectories.

In a disclosed embodiment, observing the motion includes illuminating the tip with stroboscopic illumination that is synchronized with the harmonic electric signals. Additionally, illuminating the tip includes applying multiple stroboscopic sources to illuminate the tip at different, respective frequencies with light of different, respective wavelengths.

In a further disclosed embodiment, the harmonic electrical signals include at least first and second signals having different, respective first and second frequencies, and illuminating the tip includes applying first and second stroboscopic sources to illuminate the tip at the first and second frequencies, respectively.

In another disclosed embodiment, illuminating the tip includes applying multiple stroboscopic sources to illuminate the tip from different, respective directions.

There is also provided, in accordance with an embodiment of the present invention, a medical probe. The medical probe includes a handle, a tip coupled with the handle and configured to contact tissue, and multiple piezoelectric crystals coupled with the tip of the probe so as to cause the tip to vibrate. The medical probe further includes a memory, which is configured to store an indication of respective amplitudes and phases of harmonic electrical signals for application to the multiple piezoelectric crystals so as to cause the tip to vibrate along a predefined trajectory, and control circuitry, which is configured to read the indication from the memory and to apply the harmonic electrical signals to the multiple piezoelectric crystals with the respective amplitudes and phases so as to cause the tip to vibrate along the predefined trajectory.

There is additionally provided, in accordance with an embodiment of the invention, a calibration system, including the medical probe described above and a stroboscopic illuminator that is synchronized with the harmonic electric signals applied by the control circuitry.

The present invention will be more fully understood from the following detailed description of the embodiments thereof, taken together with the drawings in which:

BRIEF DESCRIPTION OF THE DRAWINGS

FIG. 2 is a flow chart that schematically illustrates a method for calibrating a phacoemulsification probe, in accordance with an embodiment of the invention.

DETAILED DESCRIPTION OF EMBODIMENTS

Figure 1:
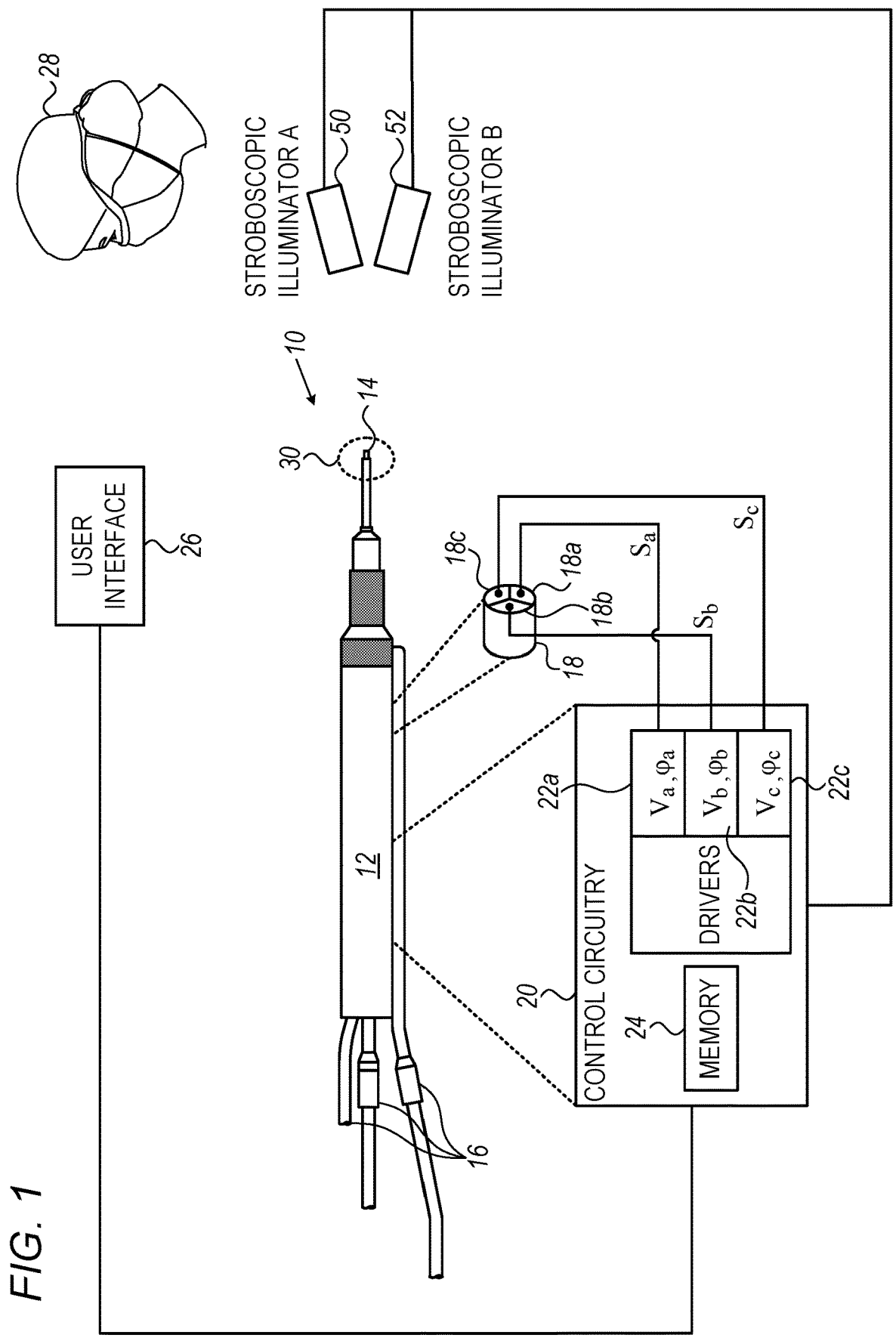
FIG. 1 is a schematic side view of a phacoemulsification probe undergoing calibration, in accordance with an embodiment of the invention.

Phacoemulsification probes are commonly capable of multiple different modes of vibration of the tip, including both linear and circular modes, for example. For this purpose, it is desirable that the mechanism responsible for vibrating the distal tip of the probe be able to vibrate independently in three dimensions (3D). This sort of vibration can be implemented using a piezoelectric transducer in the probe. #

A transducer capable of 3D motion can be made, for example, from a single piezoelectric crystal, which is cut into three or more parts. These parts are cemented together, and a pair of electrodes is attached to each part. (Alternatively, three or more separate crystals can be cemented or otherwise attached together.) This sort of device is referred to herein as a "multi-crystal." The phases and amplitudes of the drive signals that are applied to each part of the multi-crystal are chosen to generate the desired mode of vibration, such as linear or rotational motion.

Even when the multi-crystal is made by cutting a single crystal into parts, however, the different parts typically do not behave identically. For example, to vibrate an ideal multi-crystal in a circle, two pairs of electrodes could be energized with signals of the same frequency and voltage, but differing in phase by 90° so that the resultant vibrations of the parts of the multi-crystal are out of phase by 90°. In practice, the different parts of the multi-crystal have different electrical and mechanical characteristics, so that applying equal voltages with a 90° phase difference may result in a vibration trajectory that is not circular, but rather elliptical. The voltages and the phase difference needed to generate a circular trajectory are not known a priori.

The embodiments of the present invention that are described herein address this problem by carrying out a calibration procedure. For the purpose of this procedure, harmonic electrical signals are applied to the parts of the multi-crystal, and the motion of the tip is observed, for example using stroboscopic illumination. The phases and voltages of the activating signals are adjusted so as to cause the observed motion of the tip to conform to a predefined trajectory. The adjusted phase and voltage values are recorded as calibration values in a memory residing in the phacoemulsification probe. To actuate the probe to vibrate along the predefined trajectory in clinical operation, the recorded values of phases and voltages are read from the memory and applied to the multi-crystal.

FIG. 1 is a schematic side view of a phacoemulsification probe 10 undergoing calibration, in accordance with an embodiment of the invention.

Phacoemulsification probe 10 comprises a handpiece 12, a tip 14, and connectors 16 for electrical power, aspiration, and irrigation. A multi-crystal 18 drives the vibration of tip 14 in response to drive signals applied by a control circuitry 20. Multi-crystal 18 comprises three parts, i.e., three piezoelectric crystals 18a, 18b, and 18c, cemented together. Control circuitry 20 comprises three driver circuits 22a, 22b, and 22c, as well as a non-volatile memory 24, such as an electrically erasable programmable read-only memory (EEPROM). Driver circuits 22a-22c are coupled respectively with piezoelectric crystals 18a-18c, and actuate the crystals with respective harmonic signals $S_a$, $S_b$, and $S_c$, having respective amplitudes, in the form of voltages $V_a$, $V_b$, and $V_c$, and phases $\varphi_a$, $\varphi_b$, and $\varphi_c$. An external user interface 26 is coupled with control circuitry 20, enabling a user, such as a technician 28, to operate the control circuitry.

In addition to drivers 22a-22c and memory 24, control circuitry 20 comprises analog and/or digital circuits and interfaces enabling it to carry out the functions described herein. User interface 26 comprises input/output devices, for example a display screen or a touchscreen, a keyboard, a mouse, or a touchpad.

For calibrating phacoemulsification probe 10 so that tip 14 vibrates along a predefined trajectory, technician 28 commands control circuitry 20, through user interface 26, to emit signals $S_a$-$S_c$ and activate multi-crystal 18. Signals $S_a$-$S_c$ cause tip 14 to vibrate along a trajectory 30. Technician 28 observes trajectory 30, and adjusts voltages $V_a$-$V_c$ and phases $\varphi_a$-$\varphi_c$ until the trajectory conforms to the predefined trajectory. Once this conformance has been achieved, technician 28 commands control circuitry 20 to record in memory 24 an indication of the values of voltages $V_a$-$V_c$ and phases $\varphi_a$-$\varphi_c$ that yield the predefined trajectory. Subsequently, when a user, such as a surgeon, chooses to activate probe 10 so that tip 14 vibrates along this trajectory in a clinical procedure, control circuitry 20 reads the recorded values of voltages $V_a$-$V_c$ and phases $\varphi_a$-$\varphi_c$ from memory 20 and applies them to driver circuits 22a-22c in order to drive multi-crystal 18.

To assist technician 28 in observing trajectory 30, tip 14 may be illuminated with stroboscopic illumination that is synchronized with the harmonic electric signals. In many cases, a single stroboscopic illuminator, synchronized with a harmonic signal activating multi-crystal 18, is sufficient for this purpose.

In the pictured embodiment, however, two stroboscopic illuminators 50 and 52, illuminating tip 14, are coupled with control circuitry 20 in order to synchronize the stroboscopic illumination with the harmonic signals activating multi-crystal 18, wherein the phase differences between the harmonic signals and the illuminators are adjustable either stepwise or in a continuous fashion. This kind of arrangement "freezes" the vibrations of tip 14 at different points in trajectory 30, thus assisting technician 28 in adjust voltages $V_a$-$V_c$ and phases $\varphi_a$-$\varphi_c$ to achieve a desired shape of the trajectory. As the resonant frequencies of the combined multi-crystal 18 and tip 14 may be different for different modes of vibration, for example for longitudinal and transverse modes, harmonic signals $S_a$-$S_c$ may comprise more than one frequency in order to drive each vibration mode at its respective resonant frequency. For two modes of vibration, each mode may be "frozen" by synchronizing illuminators 50 and 52 with the respective resonant frequencies of the harmonic signals.

Furthermore, in order to facilitate the visual differentiation between the different vibration modes, illuminators 50 and 52 may illuminate tip 14 with light of different, respective wavelengths. For example, illuminator 50 may illuminate tip 14 with green light of wavelength of 500 nm, and illuminator 52 may illuminate the tip with red light of 600 nm. Additionally, or alternatively, illuminators 50 and 52 are positioned to illuminate tip 14 from two different directions, facilitating stereoscopic viewing of the tip and the generation of a three-dimensional (3D) image of trajectory 30 of the tip 14.

Although the pictured embodiment shows two stroboscopic illuminators, other numbers of illuminators, such as one illuminator or three or more illuminators may be used.

Alternatively, the adjustment may be carried out automatically by a computer and a suitable video camera (not shown), using techniques of image processing to measure and optimize the trajectory of tip 14. Stroboscopic illuminators 50 and/or 52 can be used in this context, as well, to facilitate image capture by the video camera. Further alternatively or additionally, other methods may be used to track the movement of tip 14.

FIG. 2 is a flowchart 100 that schematically illustrates a method for calibrating phacoemulsification probe 10, in accordance with an embodiment of the invention. The calibration is carried out by technician 28, for example, as part of a process of production and testing of probe 10. Alternatively, or additionally, the calibration process may be performed in the field. In another embodiment, the calibration process may be automated and performed as part of the production process.

Technician 28 starts the calibration in a start step 102. In a voltage and phase selection step 104, technician selects initial voltages $V_a$-$V_c$ and phases $\varphi_a$-$\varphi_c$ for signals $S_a$-$S_c$ in order to generate a certain predefined trajectory, such as a circular, rotational, or linear trajectory or combination thereof. In an activation step 106, technician 28 activates multi-crystal 18 with signals $S_a$-$S_c$. In an observation step 108, technician 28 observes trajectory 30 that is followed by tip 14, for example under stroboscopic illumination.

In a comparison step 110, technician 28 compares trajectory 30 to the predefined trajectory that the drive signals are expected to achieve. If trajectory 30 does not conform to the predefined trajectory, technician 28 adjusts the voltages $V_a$-$V_c$ and phases $\varphi_a$-$\varphi_c$ in an adjustment step 112. Multi-crystal 18 is now activated in activation step 106 using the adjusted voltages and phases from step 112. (Alternatively, the multi-crystal may be activated continuously during the calibration process.) Steps 106-112 form a control loop 113, which is iterated until trajectory 30 is found in comparison step 110 to conform to the predefined trajectory. At that time, technician 28 stores the indication of voltages $V_a$-$V_c$ and phases $\varphi_a$-$\varphi_c$ as calibration values for the predefined trajectory in memory 24, and calibration ends in an end step 116.

The calibration procedure described in flowchart 18 may be automated by using high-speed image processing, assisted by stroboscopic illumination, for example, as described above with reference to FIG. 1.

As the calibration values are stored in non-volatile memory 24, these values will be accessible after the calibration process. Thus, when a surgeon uses calibrated phacoemulsification probe 10 in a clinical procedure, he/she may select the predefined trajectory for tip 14 by a single command, and the probe will automatically apply the correct signals $S_a$-$S_c$ to multi-crystal 18.

Phacoemulsification probe 10 may be calibrated in this manner for several different modes of trajectories, such as circular, rotational, elliptical and linear (both transverse and longitudinal) trajectories. For each trajectory, the calibration procedure described in flowchart 100 is carried out separately, and the voltages $V_a$-$V_c$ and phases $\varphi_a$-$\varphi_c$ for each trajectory are stored in memory 24. Thus, during a clinical procedure, the surgeon may select any of these calibrated trajectories, and probe 10 will automatically apply the correct signals $S_a$-$S_c$ to multi-crystal 18 for that trajectory.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for calibrating a probe, the method comprising:
    applying respective harmonic electrical signals having respective amplitudes and respective phases to multiple piezoelectric crystals coupled with a tip of the probe so as to cause the tip to vibrate;
    observing a motion of the tip while applying the respective harmonic electrical signals;
    adjusting the respective amplitudes and the respective phases of the signals so as to cause the observed motion of the tip to conform to a predefined trajectory; and
    recording an indication of the respective, adjusted amplitudes and phases in a memory contained in the probe;
    wherein observing the motion comprises illuminating the tip with stroboscopic illumination that is synchronized with the harmonic electric signals; and
    illuminating the tip comprises applying multiple stroboscopic sources to illuminate the tip from different, respective directions.

2. The method according to claim 1, further comprising reading and applying the recorded indication from the memory in order to cause the probe to vibrate along the predefined trajectory in a clinical procedure.

3. The method according to claim 2, wherein the clinical procedure comprises phacoemulsification of a lens of an eye, and wherein applying the recorded indication comprises inserting the tip into a lens capsule of an eye, and vibrating the tip so as to emulsify the lens.

4. The method according to claim 1, wherein the predefined trajectory is circular.

5. The method according to claim 1, wherein adjusting the respective amplitudes and the respective phases comprises adjusting and recording the respective amplitudes and the respective phases for a plurality of different trajectories.

6. The method according to claim 1, wherein illuminating the tip comprises applying multiple stroboscopic sources to illuminate the tip at different, respective frequencies with light of different, respective wavelengths.

7. The method according to claim 6, wherein the harmonic electrical signals comprise at least first and second signals having different, respective first and second frequencies, and wherein illuminating the tip comprises applying first and second stroboscopic sources to illuminate the tip at the first and second frequencies, respectively.

8. A calibration system, comprising:
    a medical probe, comprising:
    a handle;
    a tip coupled with the handle and configured to contact tissue;
    multiple piezoelectric crystals coupled with the tip of the probe so as to cause the tip to vibrate;
    a memory, which is configured to store an indication of respective amplitudes and phases of harmonic electrical signals for application to the multiple piezoelectric crystals so as to cause the tip to vibrate along a predefined trajectory; and
    control circuitry, which is configured to read the indication from the memory and to apply the harmonic electrical signals to the multiple piezoelectric crystals with the respective amplitudes and phases so as to cause the tip to vibrate along the predefined trajectory; and a stroboscopic illuminator that is synchronized with the harmonic electric signals applied by the control circuitry;

wherein the stroboscopic illuminator comprises multiple stroboscopic sources configured to illuminate the tip from different, respective directions.

9. The system according to claim 8, wherein the stroboscopic illuminator comprises multiple stroboscopic sources configured to illuminate the tip at different, respective frequencies with light of different, respective wavelengths.

10. The system according to claim 9, wherein the harmonic electrical signals comprise at least first and second signals having different, respective first and second frequencies, and wherein the stroboscopic illuminator comprises first and second stroboscopic sources configured to illuminate the tip at the first and second frequencies, respectively.

* * * * *